United States Patent [19]

Joffe et al.

[11] Patent Number: 4,785,805

[45] Date of Patent: Nov. 22, 1988

[54] TWO-PIECE DISPOSABLE LASER DELIVERY SYSTEM

[75] Inventors: Stephen N. Joffe, Cincinnati; John Osborn, Loveland, both of Ohio; Richard L. Studer, Villa Hills, Ky.

[73] Assignee: Surgical Laser Technologies, Inc., Malvern, Pa.

[21] Appl. No.: 65,661

[22] Filed: Jun. 23, 1987

Related U.S. Application Data

[63] Continuation of Ser. No. 738,555, May 28, 1985, abandoned.

[51] Int. Cl.$^4$ .............................................. A61B 17/36
[52] U.S. Cl. .................................... 128/303.1; 128/395
[58] Field of Search ............................................ 128/4–8, 128/303.1, 395–398; 285/316, 361, 396; 403/116, 166

[56] References Cited

U.S. PATENT DOCUMENTS

| | | | |
|---|---|---|---|
| 2,529,821 | 11/1950 | Snider | 285/361 |
| 3,622,743 | 11/1971 | Munchergan | 128/303.1 |
| 3,821,510 | 6/1974 | Munchergan | 128/303.1 |
| 3,865,113 | 2/1975 | Shaeon et al. | 128/395 |
| 4,403,959 | 9/1983 | Hatakeyama | 385/316 |
| 4,503,853 | 3/1985 | Ota et al. | 128/303.1 |
| 4,519,390 | 5/1985 | Horne | 128/395 |
| 4,526,170 | 7/1985 | Tanner | 128/398 |
| 4,537,193 | 8/1985 | Tanner | 128/358 |
| 4,538,609 | 9/1985 | Tukenoka et al. | 128/395 |
| 4,552,131 | 11/1985 | Omagasi | 128/6 |
| 4,658,817 | 4/1987 | Hardy | 128/303.1 |
| 4,671,273 | 6/1987 | Lindsey | 128/303.1 |

FOREIGN PATENT DOCUMENTS 2076993 12/1981 United Kingdom .............. 128/303.1

*Primary Examiner*—Max Hindenburg
*Attorney, Agent, or Firm*—Fitch, Even, Tabin & Flannery

[57] ABSTRACT

A two component laser delivery system for surgical and endoscopic applications including a reuseable head portion for insertion into the laser generating apparatus and a disposable optic guide portion. The disposable optic guide portion is provided with a cylindrical retainer adapted to be received and locked into the reuseable portion. The reuseable portion includes a housing and a lens barrel, the lens barrel adapted to automatically retract into the housing when the disposable optic guide is removed thereby to preclude actuation of the laser interlock switch.

7 Claims, 1 Drawing Sheet

U.S. Patent  Nov. 22, 1988  4,785,805
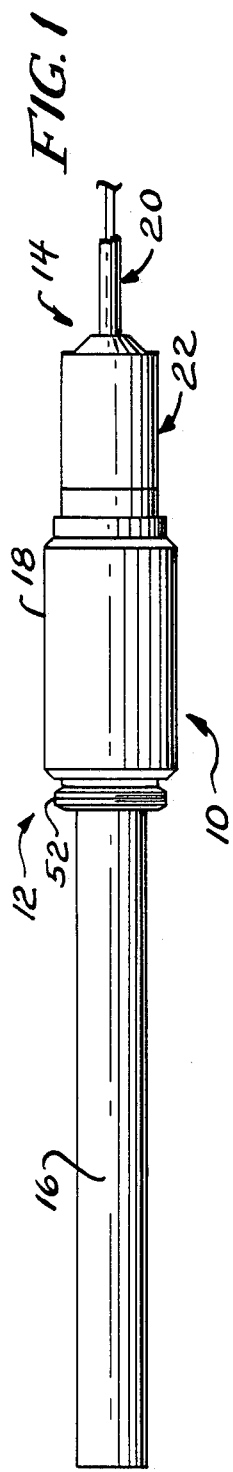
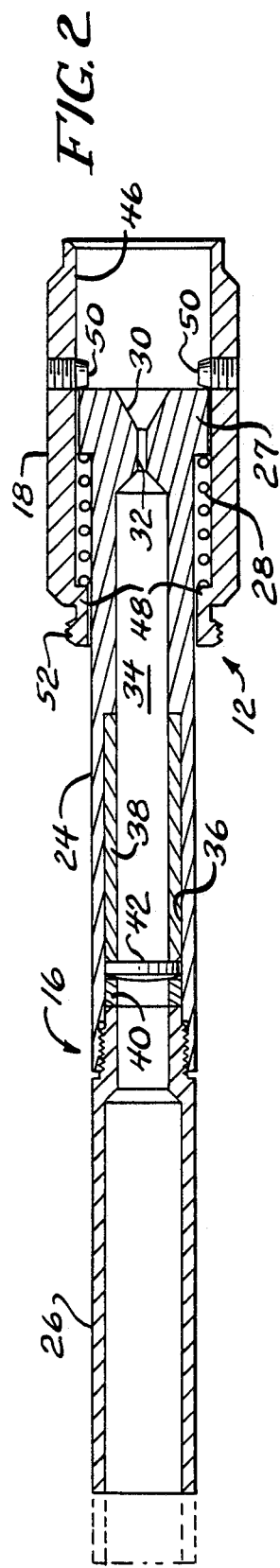
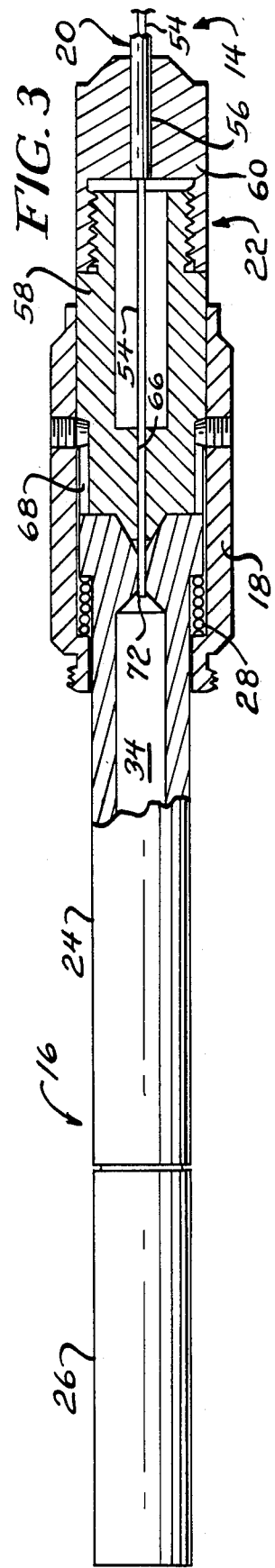
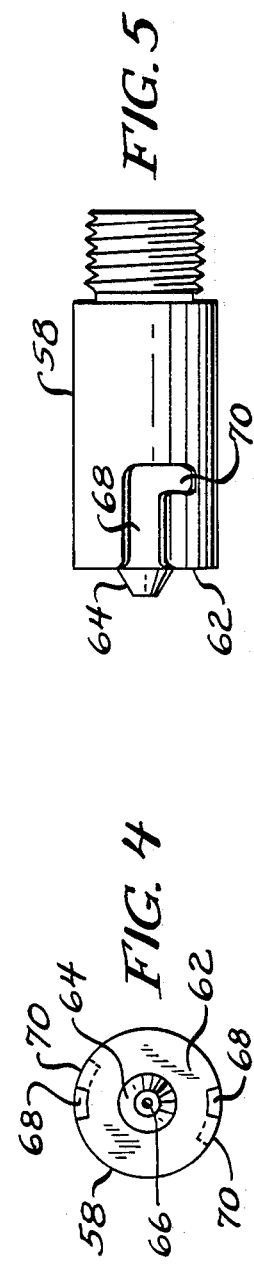

TWO-PIECE DISPOSABLE LASER DELIVERY SYSTEM

This application is a continuation of application Ser. No. 738,555, filed May 28, 1985, now abandoned.

The present invention relates to delivery systems for surgical lasers and, more particularly, to a two-piece arrangement which is both inexpensive and disposable.

Surgical lasers are typically comprised of a main chassis for generating laser energy coupled through a flexible fiber optic guide to the surgical instrument or endoscope. It is this flexible optic guide, inclusive of its interface assemblies on both the laser and instrument ends, that constitutes the delivery system.

The input interface assembly to the optic guide functions, first, as a connector to facilitate rapid removal and substitution of the optic guide during normal surgical or endoscopic use. It is not uncommon, in the course of such use, that the delivery system becomes inoperative due, either, to damage of the fiber optic guide itself, or, frequently, due to contamination of the instrument or optic fiber occasioned by the operative procedure. A replacement delivery system is then required before surgery can again commence.

Secondly, the input interface assembly must automatically trigger a laser interlock mechanism to insure that the laser cannot be operated unless properly connected to a delivery system. Typically, the interface assembly includes a head portion including a cylindrical barrel member which, when fully received within the laser unit, mechanically engages an electrical interlock switch.

Finally, the input interface assembly must focus the laser output energy onto the optic fiber which, it will be appreciated, must be accurately positioned and retained within the assembly in predetermined orientation in order to properly couple the incident laser beam. A lens is generally provided in the barrel member which receives the incident laser beam thereby focusing this beam onto the precisely located optic fiber guide.

Conventional delivery systems incorporate a factory preassembled input connector which performs the requisite functions detailed above. In addition, factory preassembly has the advantage of precision manufacture while requiring no expertise of field personnel utilizing the finished delivery system. However, conventional unitary delivery systems suffer the significant disadvantage of requiring replacement of the entire mechanism whenever the optic guide is damaged or fouled. To achieve the necessary durability and accuracy, the input interface assemblies are typically comprised of machined metal components and fittings and, further, include the costly laser focusing lens. Thus, it will be appreciated that substitution of the entire delivery system results in the replacement of expensive components which are not, themselves, damaged, but, by reason of the unitary construction of the apparatus, must be removed along with the damaged or soiled optic fiber.

The present invention pertains to a two-piece delivery system in which the a damaged optic guide may be replaced in the field without need to simultaneously interchange the expensive interface assembly components including the head portion and lens retained therein. Further, the replaceable optic guide is provided with a relatively inexpensive retainer member which results in a reduced cost optic guide portion of the delivery system generally suited for disposable use.

Proper operation of the two-piece delivery system of the present invention requires a high degree of cooperation between the reuseable and disposable portions of the system to assure proper alignment and coupling of the laser energy focused by the reuseable head member onto the disposable optic fiber positioned therein. And, importantly, the respective members must further cooperate to assure proper operation of the laser interlock whereby the laser is automatically disabled unless and until a disposable optic guide is in position. Thus, insertion of the barrel member, alone, into the laser cannot, in the conventional fashion, activate the laser while the interconnection of the disposable optic fiber member with the reuseable head must permit operation of the laser.

To facilitate the above described cooperation, the disposable optic guide is routed through the center of a generally cylindrical retainer. The diameter of this member is selected to be snugly received within the sleeve comprising the main housing of the reuseable head portion of the interface assembly. In addition, the forward surface of the retainer, from which the end of the fiber emanates, is provided with an integral raised conical region adapted to engage a complementary beveled recess in the interface barrel. In cooperation, these structural features guarantee proper fiber alignment both during initial assembly and ultimate use of the input interface assembly.

Proper interlock operation is achieved by use of a spring-loaded telescoping cylindrical barrel which partially retracts, under spring pressure, into the sleeve when the optic guide and fiber retainer are not in position. Connection of the fiber retainer forces the cylindrical barrel outwardly of the sleeve to its full extension thereby permitting actuation of the interlock mechanism upon insertion of the delivery assembly into the laser. A bayonet latch is provided to lock the disposable optical fiber and retainer in the sleeve and to properly locate the end of the fiber relative to the focused laser beam.

When it becomes necessary to replace an optical fiber, the fiber retainer is rotated to release the bayonet coupling and then withdrawn from the sleeve. If the fiber and retainer are removed with the head portion inserted in the laser, the barrel is forced outwardly, as discussed above, thereby deactivating the laser until a replacement optic guide is locked into position.

It is therefore an object of the present invention to provide a laser delivery system for surgical or endoscopic operations wherein a damaged or soiled laser optic guide or fiber may be quickly and inexpensively replaced. The delivery system shall comprise a reuseable head member and a disposable member including the fiber optic guide. It is a further object that the disposable member be field replaceable by persons of ordinary skill and that the respective reuseable head and disposable optic members incorporate a quick attachment and release arrangement, for example, a twist-lock bayonet connector. It is an object of the present delivery system that the disposable optic fiber portion of the delivery system be automatically aligned upon connection to the reuseable head member thereby facilitating the proper coupling of laser energy into the optic fiber without subsequent longitudinal or lateral adjustment of the input coupling assembly. It is a further object that head member not be able to activate the laser interlock switch unless a disposable optic assembly is affixed to the head member.

FIG. 1 is a front elevation view of the fully assembled two-piece delivery system of the present invention;

FIG. 2 is a front elevation view of the head portion of the above delivery system taken in half section showing the barrel retracted in the sleeve;

FIG. 3 is a front elevation view of the fully assembled two-piece delivery system of FIG. 1 with portions in section to reveal the relationship of the components and to illustrate the barrel in its extended position;

FIG. 4 is a horizontal view of the fiber retainer showing the bayonet latching recess; and, FIG. 5 is a left side view of the fiber retainer further illustrating the bayonet recesses and the conical fiber alignment extension.

DESCRIPTION OF THE PREFERRED EMBODIMENT

The complete laser delivery system 10 of the present invention is shown in FIG. 1. This system defines two general components, a reuseable head member 12 and a disposable optical fiber member 14. More specifically, the head member includes a cylindrical barrel 16 adapted, as detailed below, for limited longitudinal movement within sleeve 18, this sleeve also forming part of head member 12. The second component, disposable member 14, comprises the laser optical delivery fiber 20 and a fiber retainer 22 adapted to engage and lock the fiber in precise predetermined orientation within the head 12. In addition, delivery system 10 may include an operative instrument or endoscopic viewing implement, not shown, affixed to the the other terminus of fiber 20.

In normal operation, barrel 16 of the delivery system is inserted into the output port of a laser generating chassis. Upon full insertion, the barrel engages a safety interlock switch enabling laser operation and, as described in more detail below, directing laser energy into the end of the barrel (left side as viewed in FIG. 1). This energy is, in turn, coupled into the optic fiber for transmission therethrough.

FIG. 2 is a detailed illustration of head member 12 with the disposable fiber member 14 removed. Barrel 16 is comprised of lens and inner barrel sections 24 and 26, respectively, which are joined by appropriate mating threads. These barrel sections are of a substantially uniform diameter selected for proper insertion into known laser chassis output ports.

The lens barrel section 24 includes an annular ridge or lip 27 adapted for piston-like travel within sleeve 18. This lip functions, further, as a seat for compression spring 28 and a surface against which this spring operates. A beveled recess 30 is formed in the end of lens barrel 24 adjacent lip 27. Recess 30 tapers to a narrow circular channel or aperture 32 which, in turn, opens into the larger diameter main portion 34 of the barrel. Aperture 32 is precisely centered along the longitudinal axis of the barrel and is dimensioned, typically about 0.025 inches, to closely receive the optical fiber therein. In this manner, the incident laser energy may be focused directly onto the precisely located optical fiber without need for post assembly adjustment.

The inside diameter of the lens barrel is step-wise increased at the end opposite annular lip 27 to create an inner annular recess 36 adapted to receive a first and second lens spacers 38 and 40 as well as lens 42. Lens spacer 38 functions to precisely position laser focusing lens 42 a predetermined distance from the end of the optical fiber in aperture 32, the length of spacer 38 being selected in accordance with the focal length specifications of lens 42 to assure proper focusing of the laser energy onto the optical fiber. Second spacer 40 is placed in the lens barrel following insertion of the lens to assure that the lens is maintained in tight engagement against the end of spacer 38 and in perpendicular orientation to the barrel axis when the inner and lens barrels 26 and 24 are threadably engaged. The overall length of barrel 16 must be selected to guarantee activation of the laser interlock switch when the barrel is fully extended, as described below, from sleeve 18 and fully inserted into the laser output port.

Sleeve 18 defines an inner cylinder wall 46 having a diameter slightly larger than the diameter of the lens barrel lip 27 to permit the latter to travel, as noted above, in a piston-like manner therein. Movement of lens barrel 24 within sleeve 18 is limited, at one extreme, by the inwardly directed annular ridge 48 integrally formed at one end of the sleeve and, at the other extreme, by a pair of opposed bayonet locking pins 50 staked or screwed into sleeve 18. Annular ridge 48 defines a cylindrical inside surface having a diameter slightly greater than that of lens barrel 24 thereby facilitating the free, within the previously described limits, longitudinal movement of the barrel with respect to the sleeve. A compression spring 28 is positioned over the lens barrel prior to insertion into the sleeve. This spring biases the barrel toward the locking pins thereby withdrawing the barrel into the sleeve. Threads 52 are provided on the forward part of sleeve 18 adjacent the barrel which serve to engage complementary threads on the laser output port thereby to lock the laser delivery apparatus into the laser.

The second component of the present invention, the disposable optic fiber member 14, is best illustrated in FIGS. 3, 4, and 5. Disposable member 14 includes the delivery fiber 20 which, in turn, is comprised of the optical fiber 54, itself, and a sheath 56 surrounding and protecting the fiber from damage. Sheath 56 may additionally be utilized for the passage of gaseous or liquid optic fiber coolant.

Disposable member 14 further includes fiber retainer 22 which functions, not only to secure delivery fiber 20 to the laser apparatus, but importantly, as a quick attachment and release connector facilitating the required accurate orientation of the optic fiber with respect to the focused laser energy without need for further lateral or longitudinal fiber adjustment. Retainer 22 is preferably, for ease of optic fiber installation, formed of a cylindrical body 58 and cap 60 adapted to be screwed onto one end the body. The end 62 of retainer 22 opposite cap 60 is substantially planar except for an integral conical region 64 in the center thereof adapted to seat in the complementary beveled recess 30 of the lens barrel. The diameter of body 58 is substantially equal to, but slightly less than, the inside diameter of sleeve 18 thereby to assure proper centering of the retainer and fiber within the reuseable head 12. A passage 66 is provided along the center longitudinal axis of both the body and cap through which the optic fiber passes. This passage is narrowed, at least adjacent the conical end of the body, to snugly receive the optic fiber 54 thereby precisely positioning the fiber on the axis of retainer 22.

A pair of opposed L-shaped bayonet recesses 68 are provided in the outer cylindrical surface of retainer body 58. These recesses are adapted to receive pins 50 thereby to guide and lock the retainer and associated optic fiber in proper, predetermined orientation within the sleeve 18 and abutting lens barrel 24. More specifically, the longitudinal length of both recesses 68 is selected to achieve the requisite extension of barrel 16 for actuation of the laser interlock mechanism when pins 50 are properly seated in the recess ends 70. Preferably, the the width of the recess end portion 70 extends between about 5/16 and 7/16 inches from face 62 which corresponds to a barrel extension of approximately 5/16 inches upon insertion and locking of the fiber retainer 22 into the reuseable head 12.

Retainer 22 may be manufactured from machined metal components although, preferably, a molded plastic or similar material is employed in view of its reduced production cost and the disposable nature of the fiber and retainer 14. Installation of retainer 22 onto optic fiber 20 is expeditiously accomplished by removing a predetermined length of sheath 56 from fiber 54; epoxying the cap 60 to the end of the sheath; threading the exposed end of optic fiber 54 through body channel 66 until it extends outwardly from the conical projection 64; then, securing the cap to the body in convention fashion. The end of the optical fiber extends outwardly from the conical body projection as shown at 72, FIG. 3, and may be trimmed and served, as required.

As described herein, the delivery system of the present invention is comprised of two separate components, a reuseable head member 12 illustrated in FIG. 2 and a disposable optic fiber and retainer member 14 shown operatively installed in the head member in FIG. 3. Of great importance is the cooperation between these respective member whereby actuation of the laser interlock switch cannot occur until a fully assembled delivery system 10 is properly positioned in the laser output port.

Referring again to FIG. 2, it will be appreciated that spring 28 functions to maintain the barrel 16 against locking pins 50 when the fiber retainer member 22 is removed thereby retracting the barrel approximately ⅛ inch into sleeve 18. Thus, should the reuseable head be inserted into, or left in, the laser output port without the complementary optic fiber member 14 being interconnected therewith, laser operation is precluded as an additional extension of the barrel is required to actuate the interlock mechanism.

To assemble the present delivery system, the fiber retainer 22 is inserted into the open end of sleeve 18 and rotated until the longitudinal segments of bayonet recesses 68 are aligned with the respective locking pins 50. The optic fiber retainer is further advanced into the sleeve until pins 50 reach the longitudinal ends of the recesses 68 at which point the retainer is rotated to orient and lock the pins at 70. As the retainer is advanced into the sleeve, its forward face 62 contacts the lens barrel 24 thereby forcing the barrel, against spring pressure, into corresponding motion with the retainer. In this manner the barrel is extended approximately ⅛ inch relative to the sleeve.

Proper alignment of the optic fiber in relation to the focused laser beam is controlled, in the first instance, by the close fit between the retainer and the sleeve, therein, which assures that the end 72 of the optic fiber lies substantially along the axis of lens barrel 24. The beveled recess 30 of barrel 24 further assures alignment by directing the optic fiber, if initially misaligned, onto the barrel axis as the fiber is advanced into the barrel aperture 32. Once within aperture 32, proper lateral alignment of the fiber is assured by reason of the narrow diameter of that aperture. For proper longitudinal alignment, the fiber 72 extending from the conical projection is trimmed, if required, to a predetermined length which, by reason of the spring-induced tight engagement between lense barrel 24 and retainer 22, fixes the end of the fiber a corresponding predetermined distance into barrel 24. Thus, it will be appreciated that optical fibers may be virtually instantaneously replaced by unskilled personnel and without need for complicated or time consuming input assembly adjustment.

Upon installation of the optical fiber member onto the head member, the complete delivery system assembly, FIG. 3, may be inserted in conventional fashion into the output port of a laser chassis. Sleeve 18 should be rotated to threadably lock the delivery system into the laser to avoid inadvertent removal the delivery system or deactivation of the laser interlock mechanism. Once installed, however, it is not necessary to remove the complete delivery system in order to replace a faulty or soiled optic fiber. Rather, the disposable fiber portion, only, may be removed by twisting and releasing the bayonet mounted retainer from the sleeve; thereafter, inserting a replacement optic fiber assembly as previously described. Spring 28 will, as detailed above, force the lens barrel against pins 50 upon removal of the optic fiber assembly thereby automatically and instantaneously deactivating the laser interlock mechanism notwithstanding that the delivery system head member 12 remains locked to the laser chassis. In this manner, a two-piece delivery system having disposable optical fiber members may be utilized in complete safety and without fear of accidental laser operation when the complete delivery system is not in place.

We claim:

1. A laser delivery system for insertion into the output port of a laser source having a laser interlock mechanism therein, the laser source generating laser energy when the interlock mechanism is actuated, and for coupling and transmitting of laser energy therefrom through a laser optic fiber; the delivery system including a reusable portion and a generally disposable portion; the disposable portion including an optic fiber for passing laser energy and fiber retaining means on one end thereof, means for affixing the retaining means on the optic fiber whereby said one end of the optic fiber remains exposed with respect to the retaining means; the reusable portion including means for engaging the laser output port whereby laser energy from the laser source may enter the delivery system reusable portion; coacting means on the fiber retaining means and on the reusable portion for detachably coupling said reusable portion to said retaining means, the coacting coupling means including means for positioning the optic fiber and retaining means in predetermined fixed orientation with respect to the reusable portion whereby laser energy entering the reusable portion may enter the disposable portion optic fiber; said laser output engaging means including means for actuating the laser source interlock mechanism only when the disposable portion retaining means is coupled to the reusable portion; said coacting coupling means permitting attachment or removal of the disposable portion from the reusable portion by non-trained persons at the site of the laser source whereby laser energy entering the delivery system reusable portion is coupled into and transmitted through the optice fiber without adjustment of the reusable or disposable portions of the delivery system.

2. A laser delivery system for insertion into the output port of a laser source having a laser interlock mechanism therein, the laser source generating laser energy when the interlock mechanism is actuated, and for coupling and transmitting of laser energy therefrom through a laser optic fiber; the delivery system including a reusable portion and a generally disposable portion; the disposable portion including an optic fiber for passing laser energy and a cylindrical fiber retaining means on one end thereof, the retaining means having an aperture extending along a central longitudinal axis of said means, the aperture having a cross-sectional dimension adapted to receive and to position said one end of the optic fiber along the central axis of the retaining means; means for rigidly affixing said one end of the optic fiber within the retaining means aperture; the reusable portion including a body member and means operatively associated with the body member for engaging the laser output port whereby laser energy from the laser source may enter the delivery system reusable portion; coacting means on the fiber retaining means and on the reusable portion for detachably coupling said reusable portion to said retaining means, said coacting coupling means including means for positioning the optic fiber and retaining means in predetermined fixed orientation with respect to the reusable portion whereby laser energy entering the reusable portion may enter the disposable portion optic fiber, the positioning means including a cylindrical recess in the body member having a diameter substantially equal to but slightly greater than the retaining means for receiving the retaining means therein; said laser output engaging means including means for actuating the laser source interlock mechanism only when the disposable portion retaining means is coupled to the reusable portion, said coacting coupling means permitting attachment or removal of the disposable portion from the reusable portion by non-trained persons at the site of the laser source whereby laser energy entering the delivery system reusable portion is coupled into and transmitted through the optic fiber without adjustment of the reusable or disposable portions of the delivery system.

3. The laser delivery system of claim 2 wherein the reuseable portion includes a beveled recess for receiving and precisely centering said one end of the optic fiber.

4. A laser delivery system for insertion into the output port of a laser source having a laser interlock mechanism therein and for coupling and transmitting of laser energy therefrom through a laser optic fiber; the delivery system including a reuseable portion and a generally disposable portion; the disposable portion including an optic fiber for passing laser energy and fiber retaining means on one end thereof, means for affixing the retaining means on the optic fiber whereby said one end of the optic fiber remains exposed with respect to the retaining means; the reuseable portion including a barrel means for insertion into the laser output port and a body member, said barrel means extending from the body member; means for mounting the barrel means for reciprocal movement within the body member between a first extended position whereby said laser interlock mechanism may be activated and a second retracted position whereby said laser interlock mechanism may not be activated upon insertion of the barrel means into the laser output port; means biasing the barrel means to said second retracted position; coacting means on the fiber retaining means and on the body member for detachably coupling said retaining means in a predetermined fixed orientation in the body member whereby the retaining means forces the barrel to its first extended position when the retaining means is coupled to the body member and whereby the biasing means forces the barrel means to its second retracted position when the retaining means is not coupled to the body member whereby the laser interlock mechanism precludes laser operation unless the disposable and reuseable portions of the delivery system are properly coupled.

5. The laser delivery system of claim 4 wherein the means for mounting the barrel means for reciprocal movement within the body member comprises first and second cylindrical surfaces within the body member and first and second cylindrical piston surfaces on the barrel means; the first piston surface on the barrel means defining an annular ridge on one end thereof having a diameter substantially equal to, but slightly less than, the diameter of the first cylindrical surface within the body member; the second cylindrical surface in the body member having a diameter substantially equal to, but slightly greater than, the diameter of the second barrel means piston surface whereby said first and second piston surfaces are adapted for reciprocal movement within respective first and second cylindrical body member surfaces.

6. The laser delivery system of claim 4 wherein the body member includes a recess adapted to receive the retaining means therein and the coacting means for detachably coupling the retaining means in the body member includes pin means in said recess and slot means on the retaining means adapted to receive the pin means upon insertion of the retaining means into the body member recess; the slot means includes a locking region whereby positioning of the pin means therein locks the retaining means against inadvertent withdrawal from the body member; and wherein said slot means in the retaining means are defined such that the retaining means urges the barrel means to its first extended position upon the positioning of the pin means in said locking region of the slot means.

7. The laser delivery system of claim 6 wherein the means for biasing the barrel means to said second retracted position includes a compression spring which urges the barrel means against the pin means.

* * * * *